(12) United States Patent
Funamura

(10) Patent No.: US 8,475,471 B2
(45) Date of Patent: Jul. 2, 2013

(54) ORGANOPEXY TOOL AND ORGANOPEXY KIT

(75) Inventor: Shigeaki Funamura, Fukuroi (JP)

(73) Assignee: Covidien LP, Mansfield, MA (US)

( * ) Notice: Subject to any disclaimer, the term of this patent is extended or adjusted under 35 U.S.C. 154(b) by 1166 days.

(21) Appl. No.: 12/298,838

(22) PCT Filed: Apr. 28, 2006

(86) PCT No.: PCT/EP2006/004041
§ 371 (c)(1),
(2), (4) Date: Oct. 28, 2008

(87) PCT Pub. No.: WO2007/124773
PCT Pub. Date: Nov. 8, 2007

(65) Prior Publication Data
US 2009/0198257 A1    Aug. 6, 2009

(51) Int. Cl.
*A61B 17/04* (2006.01)
(52) U.S. Cl.
USPC ............................ 606/139; 606/144; 606/148
(58) Field of Classification Search
USPC ............. 606/139, 142–148, 1, 151, 213, 215, 606/221–222, 232; 604/93.01, 164.01, 170.01–170.02; 289/17
See application file for complete search history.

(56) References Cited

U.S. PATENT DOCUMENTS

| 4,006,747 | A | * | 2/1977 | Kronenthal et al. | 606/144 |
| 4,235,238 | A | * | 11/1980 | Ogiu et al. | 606/145 |
| 5,100,415 | A | * | 3/1992 | Hayhurst | 606/139 |
| 5,100,418 | A | * | 3/1992 | Yoon et al. | 606/139 |
| 5,464,426 | A | * | 11/1995 | Bonutti | 606/232 |
| 5,531,699 | A | * | 7/1996 | Tomba et al. | 604/170.02 |
| 5,562,689 | A | * | 10/1996 | Green et al. | 606/151 |
| 6,056,760 | A | * | 5/2000 | Koike et al. | 606/148 |
| 6,066,146 | A | * | 5/2000 | Carroll et al. | 606/148 |
| 6,334,446 | B1 | * | 1/2002 | Beyar | 128/898 |
| 7,875,041 | B2 | * | 1/2011 | Mikkaichi et al. | 606/144 |
| RE43,143 | E | * | 1/2012 | Hayhurst | 606/232 |
| 8,142,449 | B2 | * | 3/2012 | Kohl et al. | 606/139 |
| 2002/0050277 | A1 | * | 5/2002 | Beyar | 128/898 |

(Continued)

FOREIGN PATENT DOCUMENTS

| EP | 1 484 021 A | 12/2004 |
| JP | 63-023651 | 1/1988 |

(Continued)

OTHER PUBLICATIONS

International Search Report mailed Mar. 21, 2007 and issued by the European Patent Office in International Application No. PCT/EP2006/004041 filed Apr. 28, 2006.

(Continued)

*Primary Examiner* — Corrine M McDermott
*Assistant Examiner* — Mark Mashack

(57) ABSTRACT

Organopexy tool set (S) is comprised of suturing tool (30) comprised of rod-shaped securing section (31) and suture (32), puncture needle (10) for insertion that accommodates plural securing sections with the ends of sutures protruding to the outside, and extruding device (20) that is arranged at the base end of puncture needle for insertion and can extrude the securing section accommodated in puncture needle for insertion from an opening at the tip of puncture needle for insertion. Also, plural suture exiting holes (24) are formed at intervals around the axis on extruding device, and the ends of sutures connected to plural securing sections protrude from different suture exiting holes. In addition, extruding device (20) is equipped with extruding rod (22), friction member (29), attachment/detachment pressing section (23), and coil spring (28).

3 Claims, 10 Drawing Sheets

U.S. PATENT DOCUMENTS

| | | | |
|---|---|---|---|
| 2004/0092969 A1* | 5/2004 | Kumar | 606/151 |
| 2004/0122473 A1* | 6/2004 | Ewers et al. | 606/222 |
| 2004/0249392 A1* | 12/2004 | Mikkaichi et al. | 606/142 |
| 2004/0249395 A1* | 12/2004 | Mikkaichi et al. | 606/144 |
| 2005/0075654 A1* | 4/2005 | Kelleher | 606/151 |
| 2005/0113851 A1* | 5/2005 | Swain et al. | 606/151 |
| 2005/0234512 A1* | 10/2005 | Nakao | 606/232 |
| 2006/0271074 A1* | 11/2006 | Ewers et al. | 606/148 |
| 2007/0112359 A1* | 5/2007 | Kimura et al. | 606/142 |
| 2007/0208407 A1* | 9/2007 | Gerdts et al. | 623/1.11 |
| 2007/0276412 A1* | 11/2007 | Catanese et al. | 606/143 |
| 2009/0326561 A1* | 12/2009 | Carroll et al. | 606/148 |

FOREIGN PATENT DOCUMENTS

| | | |
|---|---|---|
| JP | 08-282180 | 10/1996 |
| JP | 2000-280683 | 10/2000 |
| WO | WO 96/09005 A | 3/1996 |
| WO | WO 03/059173 | 7/2003 |

OTHER PUBLICATIONS

Notification of Reasons for Refusal for corresponding Japanese application No. 2005126107.

* cited by examiner

ORGANOPEXY TOOL AND ORGANOPEXY KIT

TECHNICAL FIELD

The present invention pertains to an organopexy tool set used for fixing a prescribed internal organ in the body of a patient on paries.

BACKGROUND

Typical prior art organopexy tool sets are used to fix a sutured part, especially, paries and an internal organ in a patient body. For example, for those who are unable to eat food by mouth due to old age or disease, a gastrostomy tube is used to supply fluid food or nutrients. The gastrostomy tube is installed after a hole (gastrostoma) is formed in the stomach area of the patient. In this case, in order to install the gastrostomy tube properly, it is necessary to use an organopexy tool set to fix the abdominal wall and the gastric wall in advance (for example, see Patent Reference 1). A prior art gastrostomony tube device is found in U.S. Pat. No. 6,458,106 of Meier, granted Oct. 1, 2002 presently owned by the assignee of the present invention.

The Kokai organopexy tool set has two puncture needles set at an interval and in parallel (cf. Japanese Patent Application No. Hei 5[1993]-161655 of Kokai). To fix the abdominal wall and the gastric wall, a suture is inserted into one of the puncture needles, and an inner needle with a loop unit connected to the tip part is inserted into the other puncture needle. The inner needle is pulled out of the puncture needle with the suture held by the loop unit inside the stomach wall. Then, with the tip part of the suture projecting from the opening at the base end of the other puncture needle, the two puncture needles are pulled out of the abdominal part, and the two parts of the suture sticking out of the patient's body are tied to complete fixing of the abdominal wall and the stomach wall.

SUMMARY OF THE INVENTION

For the prior art organopexy tool set, the two puncture needles must puncture at the same time, and it is necessary to insert the inner needle and the suture into the puncture needles. Complications occur if the inner needle is not inserted into the puncture needle properly, or the projecting direction or shape of the loop unit may not be correct to hold the suture. Other problems occur if there is not enough space on the inner side of the organ, as it is difficult to hold the suture by the loop unit, and the probability of catching the suture in the loop unit is low. The present invention solves this other problems over the more complicated prior art devices as shown in the Japanese Patent Application No. Hei 5[1993]-161655 of Kokai.

The objective of the present invention is to solve the aforementioned problems by providing an organopexy tool set which can fix an organ reliably in a simple one step operation.

An objective of the present invention is to provide an organopexy tool set used for fixing a prescribed internal organ on paries, characterized by having the following: a rod-shaped securing section, a suturing tool comprised of sutures connected to approximately the central part of the securing section in the axial direction, a puncture needle for insertion that is made from a cylindrical body with a sharp end and sized to accommodate the securing section within the puncture needle, and the non-connected ends of the sutures project to the outside from the base end part of the cylindrical body, and an extruding device that is arranged at the base end of the puncture needle that is suitable to repeatedly extrude the securing section accommodated in the puncture needle at a prescribed pitch from the opening at the tip of the puncture needle.

The organopexy tool set disclosed in the present invention is equipped with a suturing tool, puncture needle for insertion, and an extruding device. The suturing tool is comprised of a rod-shaped securing section arranged on the side of the inner wall of the organ and sutures that extend out of the patient body from the center of the securing unit through the hole formed on the patient. In this case, approximate center in the axial direction of the securing section refers to the approximate center in the length direction of the securing section. When the securing section is positioned inside the organ, the securing section is open with respect to the fixing part. The securing section and the fixing part form a T. After the securing section is positioned inside the organ, the securing section is along the inner wall of the organ, and the part of the suture on the free end sticks out of the body. This allows a pair of suturing tools to be installed on the patient body, and the sutures of the two suturing tools are suitable to be tied to form a suture to fix the organ on the paries. This reduces complications and simplifies the operation of the suture tool.

The securing section fits into the puncture needle with the axial direction of the securing section aligned with the securing section of the puncture needle. The securing section is suitable to be repeatedly extruded by the extruding device at a prescribed pitch from the opening at the tip of the puncture needle. By setting the prescribed pitch according to the length of the securing section, the securing section is suitable to be extruded from the opening at the tip of the puncture needle in single operation.

Another feature of the organopexy tool set disclosed is that a plural of suturing tools can fit in puncture needle. This allows for a plural of securing sections to be parallel to the axial direction inside the puncture needle. The plural securing sections are suitable to be sequentially extruded by the extruding device from the opening at the tip of the puncture needle. It is understood two, four or more than four securing sections can be arranged in the puncture needle for insertion. The suturing tools are installed sequentially in the puncture needle that pierces the body part to be sutured. This avoids re-setting the suturing tool in the puncture needle each time a suturing tool is installed on the patient body. Since the operation can be repeated consecutively for a number of times equal to the number of suturing tools, the operation for installing the suturing tools in a patient body is simplified.

Another feature of the organopexy tool set disclosed is that a plural of suture exiting holes are made at certain intervals around the axis of the puncture needle at its base end, and the non-connected ends of the sutures connected to the securing sections are projected to the outside from different suture exiting holes, respectively. In this way, even if plural sutures are set in the puncture needle for insertion, so the suture threads will not tangle since each suture is positioned at a different point around the axis of the puncture needle. Each securing section can be extruded from the puncture needle and installed in the patient body. Instead of the part on the side of the base end of the puncture needle for insertion, it is also possible to form the suture exiting holes on the puncture needle for insertion or on the extruding device.

Another feature of the organopexy tool set disclosed is the extruding device. The extruding device is comprised of a cylindrical handle section that is formed on the side of the base end of the puncture needle, and the device is connected to the puncture needle on the inside, an extruding rod that can move between the interior of the cylindrical handle section and the interior of the puncture needle, and a friction surface that is arranged on the cylindrical handle section or extruding rod that is suitable to apply a prescribed frictional force to the extruding rod moving in the cylindrical handle section.

The friction part is constructed such that the inner peripheral surface of the cylindrical handle section contacts the extruding rod, and the inner peripheral surface of the cylindrical handle section or the peripheral surface of the extruding rod is formed into the frictional surface. The friction part can also be formed by arranging rubber or another material that can generate friction in the cylindrical handle section. When no pressing force is applied, the extruding rod is held by the friction part and stays still in the cylindrical handle section. When the pressing force exceeds the frictional force of the friction part, the extruding rod is pressed into the puncture needle for insertion to extrude the securing section in the puncture needle for insertion toward the opening at the tip of the puncture needle for insertion. When the extruding rod is pressed by the length of the securing section, the extruding rod will advance to the tip part in the puncture needle for insertion to extrude the securing section to the outside.

The organopexy tool set disclosed has the following features. A hold releasing part is formed on the tip side which is positioned on the side of the puncture needle inside the cylindrical handle section. The hold sustaining part is closer to the base end than the hold releasing part inside the cylindrical handle section. The friction part is made of a frictional member having an elastic hole, through which the extruding rod is inserted, and is positioned closer to the puncture needle than the hold releasing part inside the cylindrical handle section.

The organopexy tool set is also equipped with an attachment/detachment pressing section, which is arranged movably in the cylindrical handle section with the extruding rod inserted inside. The base end part of the pressing section is constructed by a pressing part projecting from the cylindrical handle section. The tip part of the pressing section is constructed by a holding part that can hold the extruding rod when pressed by the hold sustaining part and can release the extruding rod when pressed by the hold releasing part. The organopexy tool set is also equipped with an energizing member, which is arranged in the cylindrical handle section and energizes the attachment/detachment pressing section away from the puncture needle. The extruding device is configured as follows: the pressing part is pressed against the energizing force of the energizing member with the holding part pressed by the hold sustaining part to hold the extruding rod, the attachment/detachment pressing section moves toward the puncture needle along with the extruding rod and when pressing of the pressing part is stopped with the holding part pressed by the hold releasing part to release the extruding rod, along with the extruding rod held by the friction member, the attachment/detachment pressing section moves away from the puncture needle under the energizing force of the energizing member.

The extruding rod can be repeatedly inserted into the puncture needle for insertion at a prescribed pitch. If the pitch is set according to the length of the securing section, the securing section is suitable to be extruded from the tip of the puncture needle by pressing the extruding part once. In this case, the interval between the hold releasing part and the hold sustaining part can be set to the prescribed pitch. Also, if a plural of securing sections are arranged in the puncture needle, a securing part is extruded from the tip of the puncture needle each time the pressing part is pressed. This continuous operation is carried out easily and correctly.

Other features of the organopexy tool set disclosed include the following. The holding part is comprised of a cylindrical body comprised of plural holding pieces formed with the tip part diverging toward the outer periphery and a fastening tool, which is installed movably on the outer peripheral surface of the cylindrical body, and which can fasten the holding pieces toward the axis side to hold the extruding rod when it is positioned at the tip of the cylindrical part and can release the extruding rod by the holding pieces when it is positioned closer to the base end than the holding pieces on the cylindrical body.

BRIEF DESCRIPTION OF THE FIGURES

Preferred embodiments of the present invention will now be described, by way of example only, with reference to the accompanying drawings in which.

DETAILED DESCRIPTION OF PREFERRED EMBODIMENTS OF THE INVENTION

Figure 1:
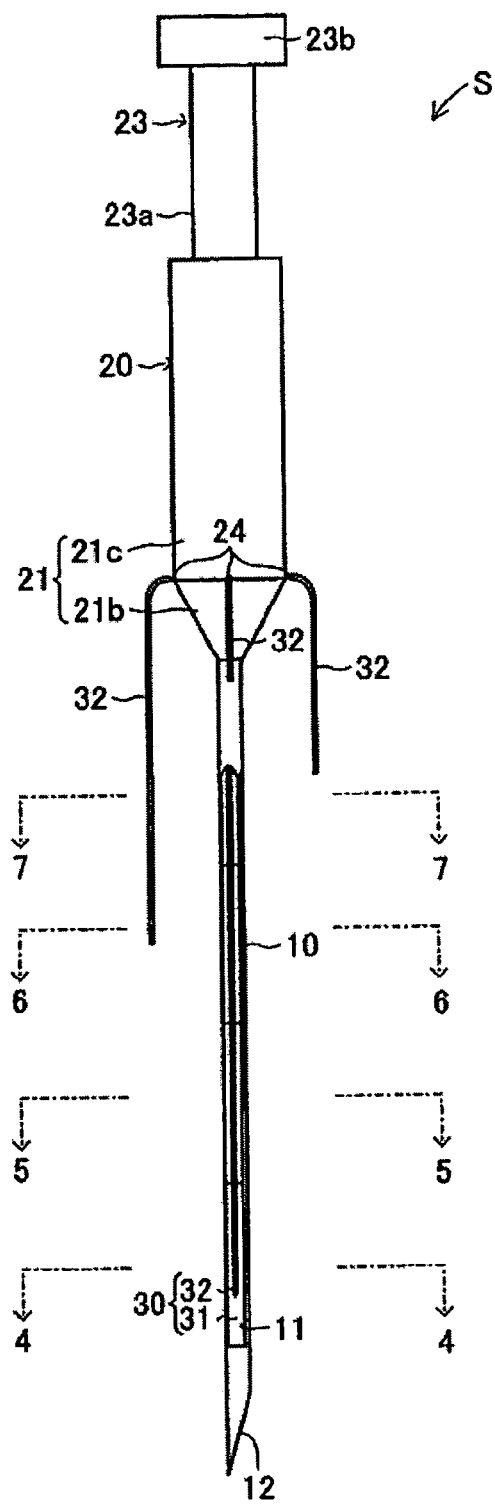
FIG. 1 is a partially cut front view illustrating the organopexy tool set disclosed in an embodiment of the present invention.

The preferred embodiment of the present invention is disclosed describing the invention as set forth in the FIGS. 1-15. FIG. 1 shows an organopexy tool set S of the present invention. The organopexy tool set S, for example, is used to suture and fix stomach wall B (see FIGS. 8, 9, 11) on abdominal wall A of a patient. The tool set S is comprised of a puncture needle 10, an extruding device 20 installed at the base end (upper end in FIG. 1) of puncture needle 10, and four suturing tools 30 (shown in this embodiment) are positioned in the puncture needle 10. The puncture needle 10 is further composed of a metal cylindrical body with an insertion hole 11 formed inside. A tip part 12 of puncture needle 10 is cut at an oblique direction with respect to the axial direction to a sharp. The opening part is formed to face horizontally.

Figure 2:
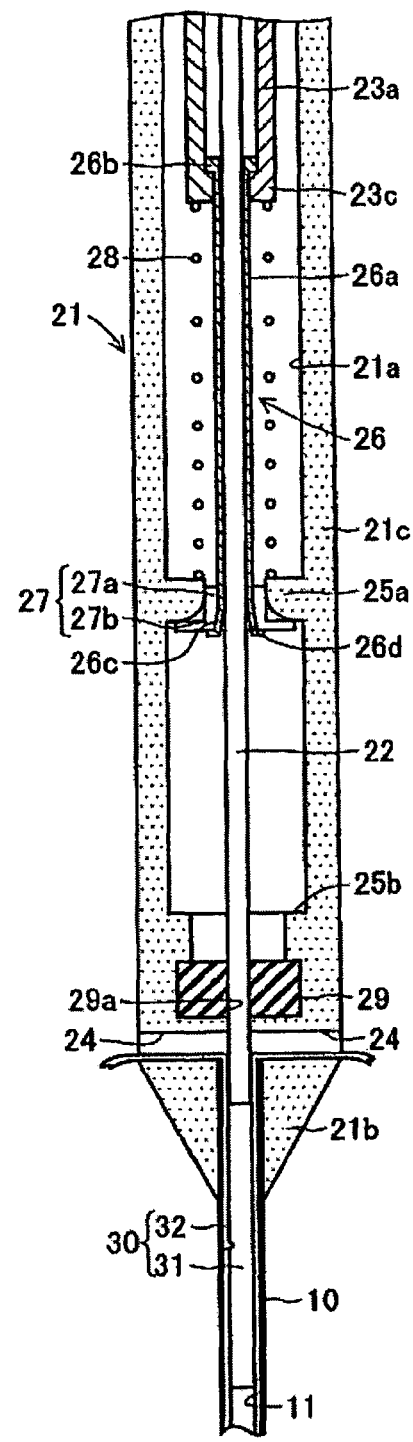
FIG. 2 is a cross-sectional view illustrating the interior of the extruding device in the organopexy tool set shown in FIG. 1.
Figure 10:
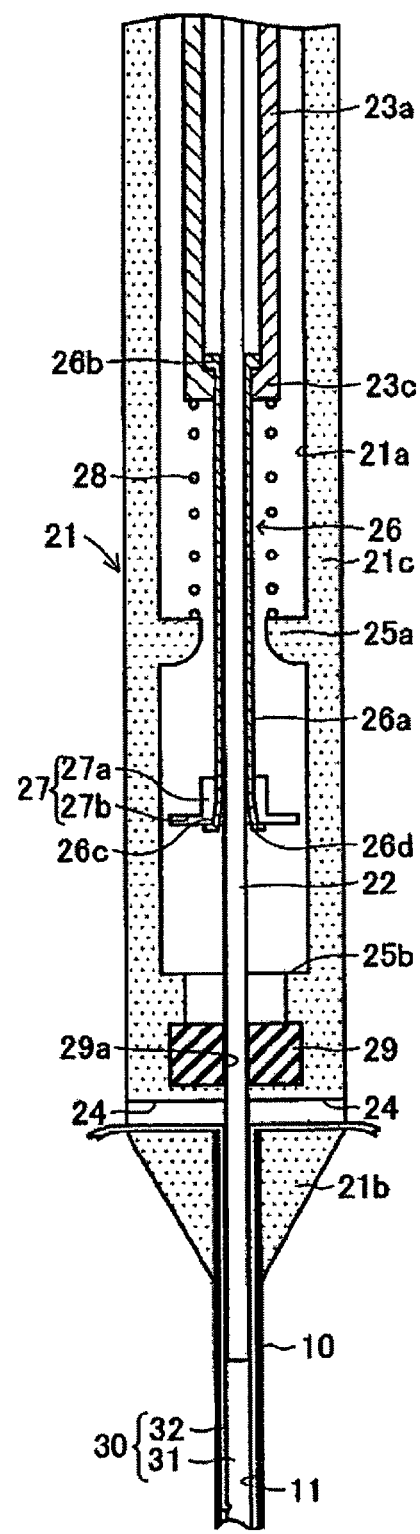
FIG. 10 is a cross-sectional view illustrating the state when the attachment/detachment pressing section descends in the extruding device.

Referring to FIGS. 2 and 10, the extruding device 20 is comprised of a cylindrical handle section 21 fixed at the base end part of puncture needle 10, an extruding rod 22, and an attachment/detachment pressing section 23. The cylindrical handle section 21 is constructed of a plastic cylindrical body, while other materials such as metal can be sued. A space part 21a formed inside the cylindrical handle section 21 is connected to the insertion hole 11 of puncture needle 10. An opening (not shown in the figure) to the outside is formed on the upper end surface of cylindrical handle section 21. The lower end part of cylindrical handle section 21 is formed by a conical connection part 21b that converges toward the bottom. Cylindrical handle section 21 is assembled with puncture needle 10 by fixing the connection part 21b in the base end part of puncture needle 10.

Referring to FIGS. 1 and 2, the four suture exiting holes 24 are formed circumferentially at the boundary part of main body side part 21c and connection part 21b of cylindrical handle section 21. A pedestal 25a is serving as the hold sustaining part. The pedestal 25a is formed in the lower part of the inner peripheral surface of cylindrical handle section 21 and projects to the central axis side of cylindrical handle section 21. A hold releasing part 25b is a step part with a diameter smaller than that of space part 21a. The hold releasing part 25b is formed at the lower end of the inner peripheral surface of main body side part 21c. An extruding rod 22 is made of metal or similarly constituted material. The extruding rod 22 is moved between the insertion hole 11 of puncture needle 10 and the space part 21a of cylindrical handle section 21.

An attachment/detachment pressing section 23 is comprised of a plastic cylindrical main body part 23a, into which the extruding rod 22 can be inserted movably, a disk-shaped pressing part 23b formed integrally with the upper end of main body part 23a, and metal holding part 26 fixed to the lower end of main body part 23a. The attachment/detachment pressing section 23 is movably in the cylindrical handle section 21 with pressing part 23b projecting to the outside from the opening at the upper end of cylindrical handle section 21. An engagement step part 23c, with smaller inner diameter than inside the cylindrical handle section 21, is formed in the lower end part of the inner peripheral surface of main body part 23a.

Referring to FIG. 2, a holding part 26 is comprised of cylindrical body 26a, through which extruding rod 22 can pass while moving, and fastening tool 27 (made of a metal) is installed at the lower end of cylindrical body 26a. A flange-shaped engagement part 26b is formed in the upper end part of cylindrical body 26a. The holding part 26 is installed on the main body part 23a with said engagement part 26b engaged with engagement step part 23c. Also, the lower end part of cylindrical body 26a is comprised of four holding pieces 26c spaced at equal intervals around the axis. A projection 26d projecting outward is formed at the lower end of each holding piece 26c. The holding pieces 26c are formed to be energized such that they expand outwards. The holding pieces 26c under a force are pressed toward the central axis and under this force the holding pieces press against extruding rod 22 to hold it in place.

Referring to FIG. 2, the fastening tool 27 is comprised of cylindrical fastening part 27a with a short length in the axial direction and flange-shaped fastening release piece 27b formed on the outer periphery of the lower end of fastening part 27a. The diameter of fastening part 27a is set so that the fastening part can enter the central hole of pedestal 25a. Moving the attachment/detachment pressing section 23 upwards causes the fastening part 27a to enter the central hole of pedestal 25a. This upward action moves fastening tool 27 to the lower end of cylindrical body 26a to fasten holding pieces 26c to the axial side. The diameter of fastening release piece 27b is larger than the central hole of holding release part 25b. Moving the attachment/detachment pressing part 23 downward causes the fastening release piece 27b to press against holding release part 25b. This downward action moves the fastening tool 27 higher than the lower end of cylindrical part 26a to release the fastening force on holding pieces 26c. Upon release of the force, the holding pieces 26c expand outward to release its hold on the extruding rod 22.

Referring to FIG. 2, a coil spring 28 is used for energizing attachment/detachment pressing section 23 upwards with respect to cylindrical handle section 21. The coil spring 28 is set on the side of the outer periphery of cylindrical body 26a between the top surface of pedestal 25a in cylindrical handle section 21 and the bottom surface of main body part 23a. A friction member 29, made of rubber, is set at the lower end of the central hole of hold releasing part 25b in cylindrical handle section 21. An elastically deformable through-hole 29a is formed at the center of friction member 29. The extruding rod 22 passes through the hole 29a under a prescribed frictional force applied to the extruding rod (22).

The rubber friction member 29 frictional force is set to be smaller than the force by holding part 26 that holds extruding rod 22. Pushing the attachment/detachment pressing section 23 downward, with holding part 26 holding extruding rod 22, the extruding rod 22 moves downwards along with attachment/detachment pressing section 23, and coil spring 28 shrinks. At the same time, the holding part 26 is pressed against hold releasing part 25b, and the force by holding part 26 holding extruding rod 22 is released. Releasing the downward force against attachment/detachment pressing section 23, the coil spring 28 extends, and the attachment/detachment pressing section 23 moves upwards. After the force dissipates, the extruding rod 22 is held by friction member 29 in a stationary position.

Figure 3:
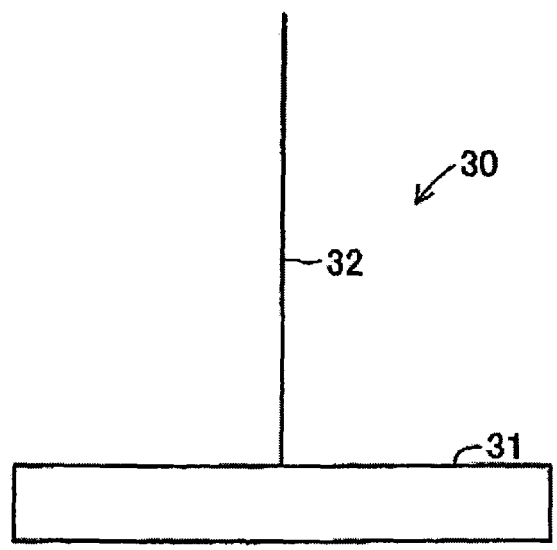
FIG. 3 is a front view illustrating the suturing tool of the organopexy tool set shown in FIG. 1.
Figure 4:
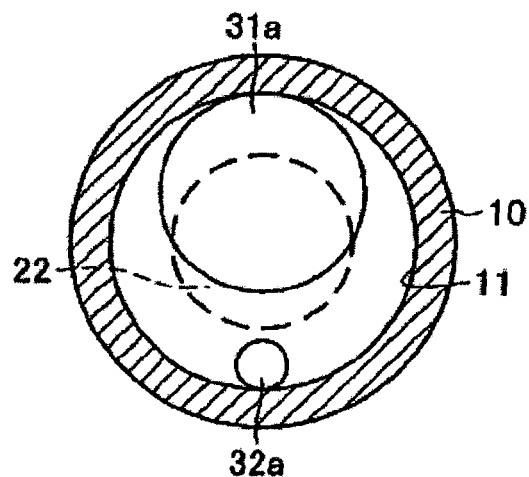
FIG. 4 is a cross-sectional view along 4-4 in FIG. 1.

As shown in FIG. 3, suturing tool 30 is comprised of rod-shaped securing section 31 made of metal and suture 32 made of nylon. The suture 32 extends from the central part of securing section 31 axially in the direction perpendicular to securing section 31. The securing section 31 and suture 32 can be connected to each other, for example, by forming an annular groove on the peripheral surface of securing section 31 and forming the tip end part of suture 32 in a ring and fitting the tip end part of suture 32 in the groove of securing section 31. It is also possible to form a through-hole or an engagement hole recessed and perpendicular to the axial direction in securing section 31 and connect suture 32 to securing section 31 using the through-hole or engagement hole.

Figure 5:
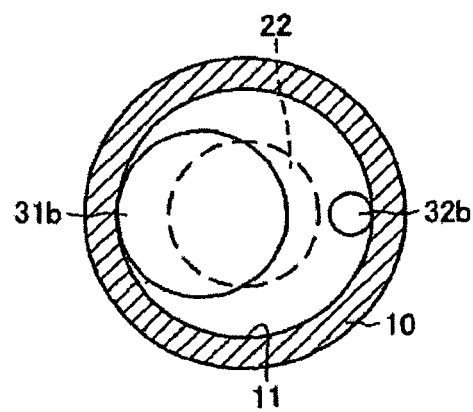
FIG. 5 is a cross-sectional view along 5-5 in FIG. 1.

Referring to FIG. 1 at cross sections 4-7, the four suturing tools 30 are positioned in the puncture needle 10 with each securing section 31 parallel to the axial direction of puncture needle 10 and each suture 32 arranged at a certain interval around the axis of puncture needle 10. FIGS. 4-7 show the cross sections 4-7 positions of the securing section 31 and suture 32 of suturing tool 30 set starting at the tip 12 (lowest part) of puncture needle 10. Comparing FIG. 1 with FIG. 4, securing section 31 is taken as securing section 31a and suture 32 is taken as suture 32a, suture 32a is positioned on the front side, while securing section 31a is positioned on the back side in puncture needle 10. As shown in FIG. 5, if the securing section 31 and suture 32 of the suturing tool 30 set at the second position from the bottom in puncture needle 10 are taken as securing section 31b and suture 32b, suture 32b is positioned on the right side, and securing section 31b is positioned on the left side in puncture needle 10 for insertion shown in FIG. 1.

Figure 6:
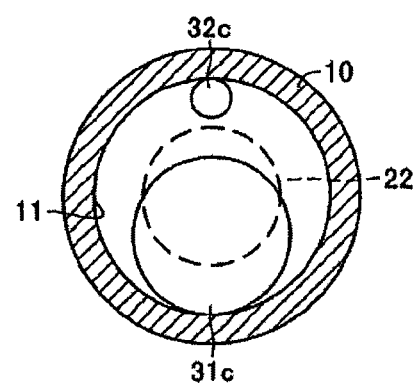
FIG. 6 is a cross-sectional view along 6-6 in FIG. 1.
Figure 7:
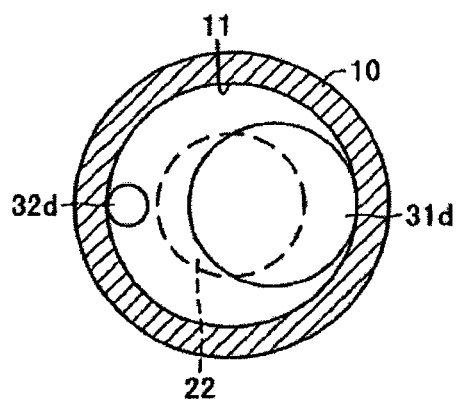
FIG. 7 is a cross-sectional view along 7-7 in FIG. 1.

As shown in FIG. 6, if the securing section 31 and suture 32 of the suturing tool 30 set at the third position from the tip 12 of puncture needle 10 for insertion are taken as securing section 31c and suture 32c, suture 32c is positioned on the back side, and securing section 31c is positioned on the front side in puncture needle 10 for insertion shown in FIG. 1. As shown in FIG. 7, if the securing section 31 and suture 32 of the suturing tool 30 set at the highest position in puncture needle 10 for insertion are taken as securing section 31d and suture 32d, suture 32d is positioned on the left side, and securing section 31b is positioned on the right side in puncture needle 10 for insertion shown in FIG. 1.

Figure 8:
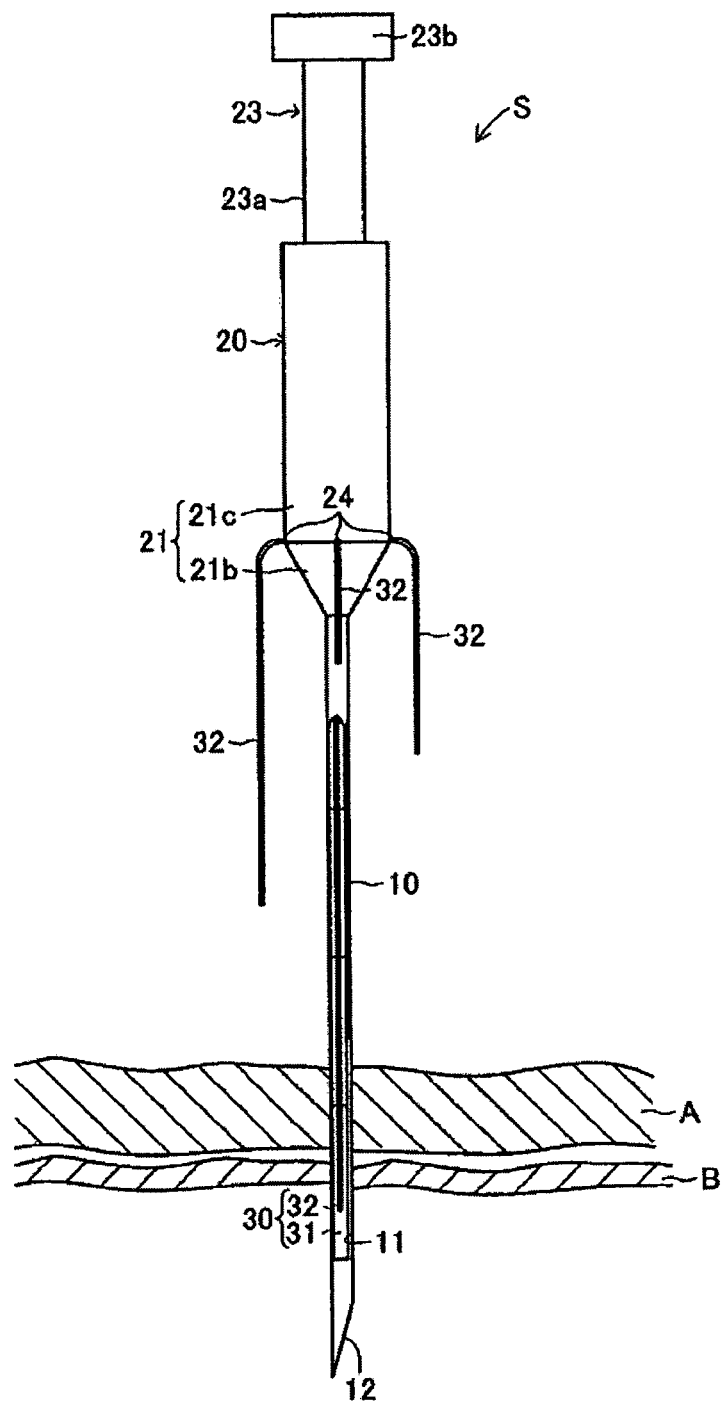
FIG. 8 is a cross-sectional view illustrating the state when the organopexy tool set shown in FIG. 1 pierces into the abdomen.

As shown in FIG. 8, the free end of each suture 32 projects outside through suture exiting hole 24 positioned in the cylindrical handle section 21. Each suturing tool 30 is set such that the lower end of securing section 31a set on the side of tip 12 of puncture needle 10 is positioned at the upper end of the opening at the tip 12 of puncture needle 10 for insertion, and the lower end of extruding rod 22 contacts the upper end of securing section 31d set on the side of the base end of puncture needle 10 for insertion.

A method of using organopexy tool set S to suture abdominal wall A to stomach wall B of a patient will now be explained. As shown in FIG. 8, puncture needle 10 for insertion pierces into abdominal wall A and stomach wall B by pressing organopexy tool set S on the skin surface in the abdominal area of the patient. The organopexy tool set S is pressed inward until the opening at the tip 12 of puncture needle 10 for insertion reaches the interior of stomach wall B. At the interior of stomach wall B, the interior of extruding device 20 is shown in FIG. 2. The pressing part 23b is pressed with respect to cylindrical handle section 21 to press attachment/detachment pressing section 23 into cylindrical handle section 21 to reach the configuration shown in FIG. 9.

Figure 9:
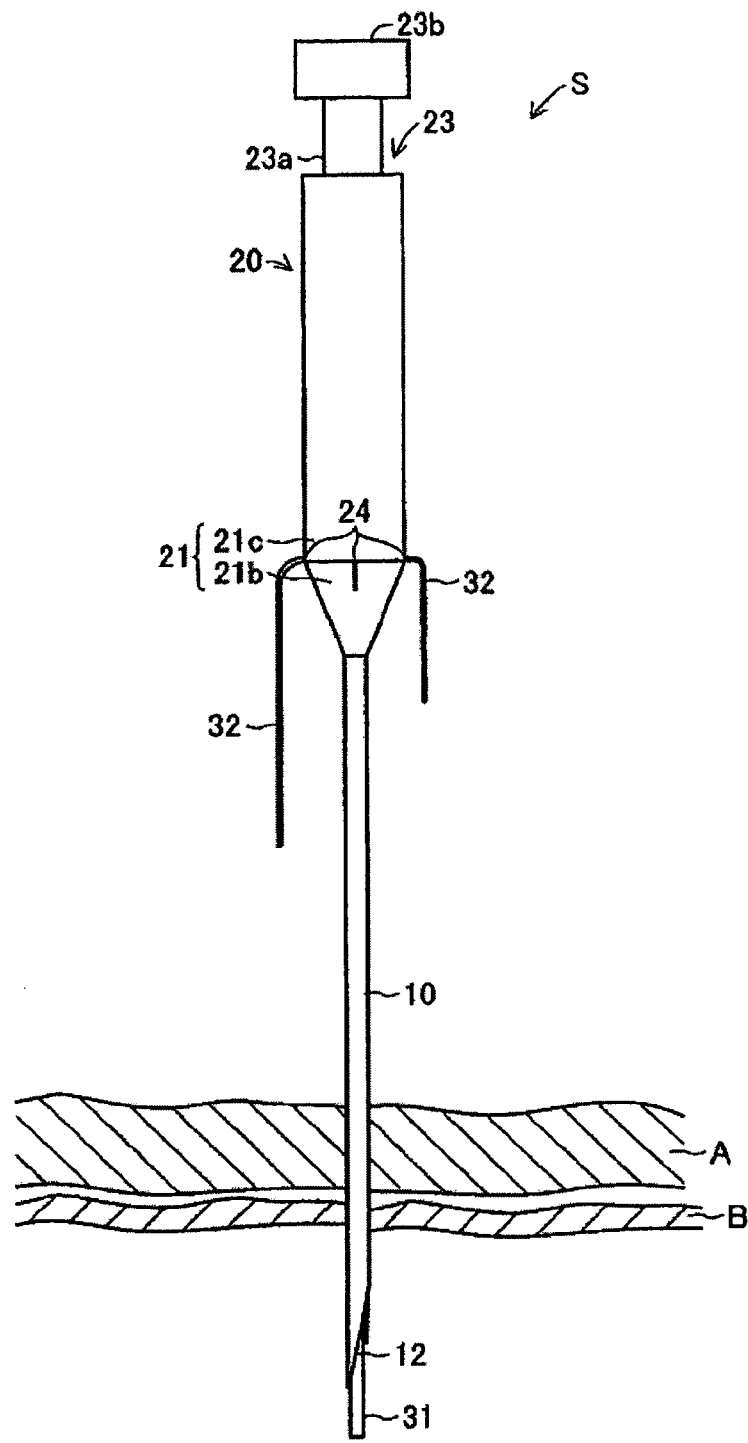
FIG. 9 is a cross-sectional view illustrating the state when the securing section is extruded from the tip part of the puncture needle.

Referring to FIG. 9, the lowest securing section 31 protrudes from the tip part 12 of puncture needle 10, and the amount of suture 32 protruding from each suture exiting hole 24 is shortened by the movement distance of pressing part 23b. The attachment/detachment pressing section 23 is pressed into cylindrical handle section 21 as shown in FIG. 10 from the configuration shown in FIG. 2. Referring to FIG. 9, the fastening tool 27 holding extruding rod 22, moves downwards along with extruding rod 22 under the force applied to pressing part 23b, and each securing section 31 is pressed downwards by the movement of extruding rod 22. As the force continues, the coil spring 28 compresses further a corresponding amount to the distance traveled of extruding rod 22, etc.

Figure 11:
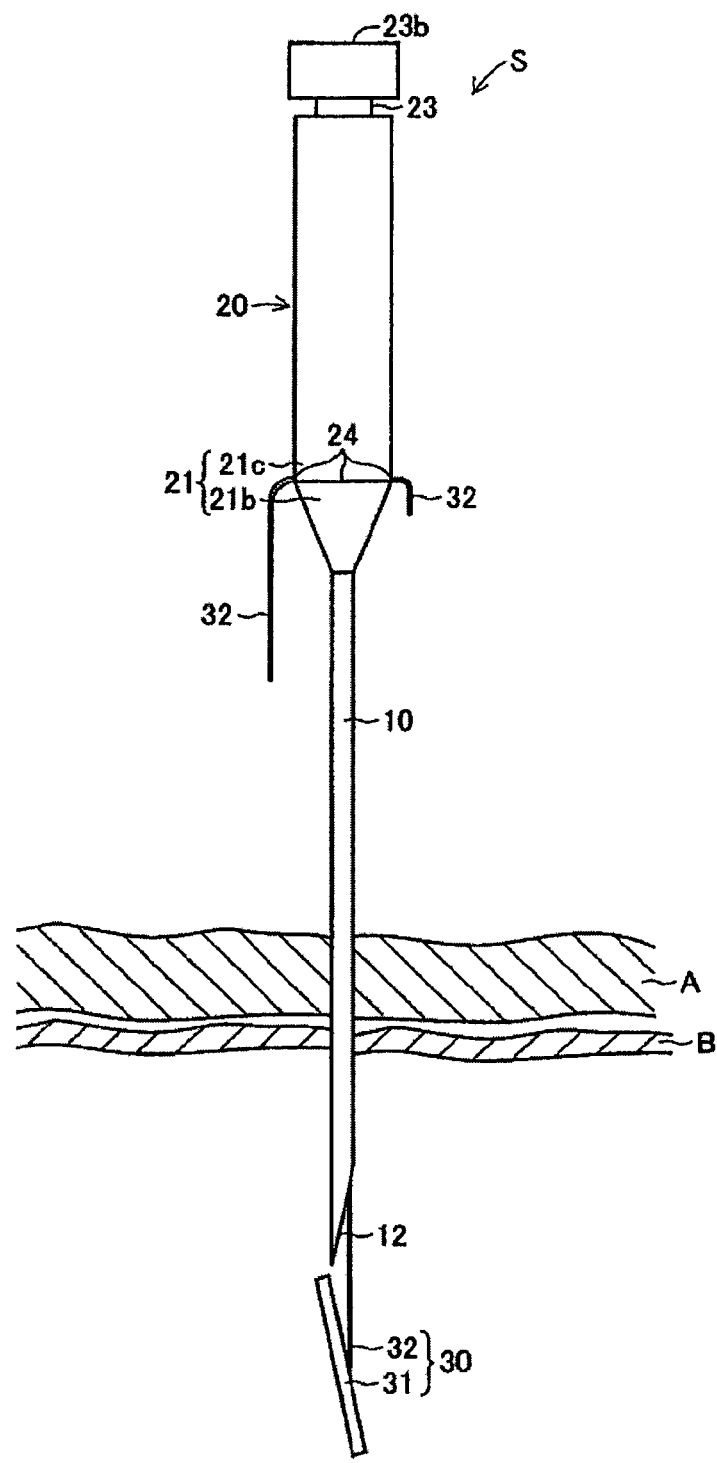
FIG. 11 is a cross-sectional view illustrating the state when the securing section is extruded from the tip part of the puncture needle.
Figure 12:
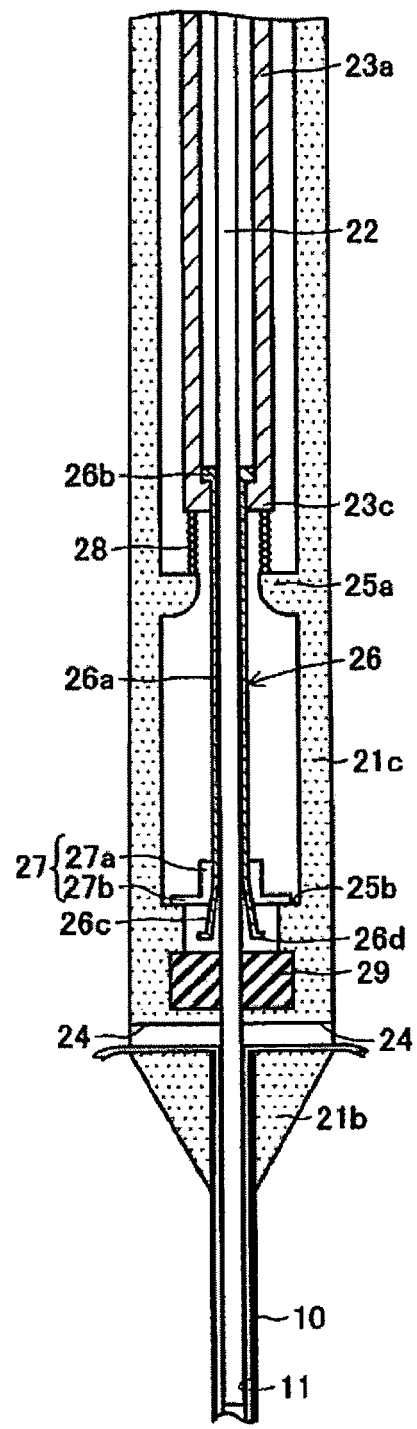
FIG. 12 is a cross-sectional view illustrating the state when the attachment/detachment pressing section descends in the extruding device to release the extruding rod.

Upon further force applied to pressing part 23b, the attachment/detachment pressing section 23 is pressed into cylindrical handle section 21, as shown in FIG. 11. After a sufficient amount of force is applied, the lowest securing section 31 is pressed out of puncture needle 10 and is positioned inside stomach wall B. The configuration of attachment/detachment pressing section 23 after it is further pressed into cylindrical handle section 21 is shown in FIG. 12 from the configuration shown in FIG. 10. A securing suture 31 is placed and the coil spring 28 is compressed to its minimum length. The fastening release piece 27b of fastening tool 27 moves to the position of hold releasing part 25b. The fastening tool 27 is holding extruding rod 22, as the fastening tool 27 moves downwards, as shown in FIG. 12.

For the next securing suture 31, the lower end of extruding rod 22 remains in contact with the top surface of the next highest securing section 31. The holding of extruding rod 22 by fastening tool 27 is released when the fastening release piece 27b of fastening tool 27 is pressed against hold releasing part 25b, fastening tool 27 moves to the side of the upper part of holding piece 26c on cylindrical body 26a. Upon release of the force from pressing part 23b, the attachment/detachment pressing part section 23 returns to the original position (state shown in FIG. 2) under the recovering force of compressed coil spring 28. At that time, extruding rod 22 is held by the frictional force of friction member 29 and remains stationary without going up.

Figure 13:
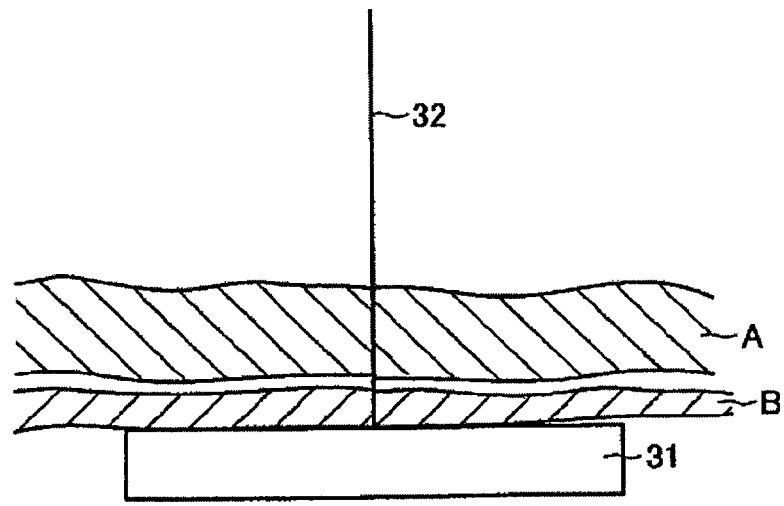
FIG. 13 is a cross-sectional view illustrating the state when the securing section is engaged with the inner part of the stomach wall.

Upon release of the force at pressing part 23b, the fastening part 27a of fastening tool 27 is rising inside cylindrical handle section 21. The positioned of fastening tool 27 inside the central hole of pedestal 25a, prevents fastening tool 27 from rising by pedestal 25a and moves to the side of the holding pieces 26c of cylindrical body 26a to fasten holding pieces 26c to the axial side. The extruding rod 22 is held by holding part 26. The user removes the organopexy tool set S from the body of the patient. With the suture thread 32 still intact, the securing section 31 extruded to the inner side of stomach wall B is extended in the horizontal direction along stomach wall B as shown in FIG. 13 and is engaged with stomach wall B. The securing section 31 is removed from organopexy tool set S and is left inside the body of the patient. After the extruding of the first securing section 31, the remaining three securing sections 31 are left in puncture needle 10 for insertion at a later time. The lower end of the lowest securing section 31 is positioned at the top of the opening at the tip 12 of puncture needle 10 for the next insertion.

Figure 14:
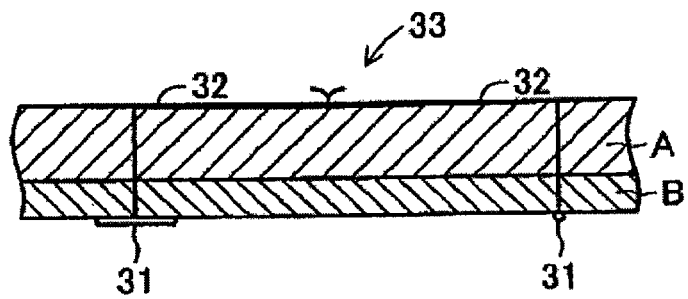
FIG. 14 is a cross-sectional view illustrating the state when the stomach wall is fixed on the abdominal wall by the sutured part.
Figure 15:
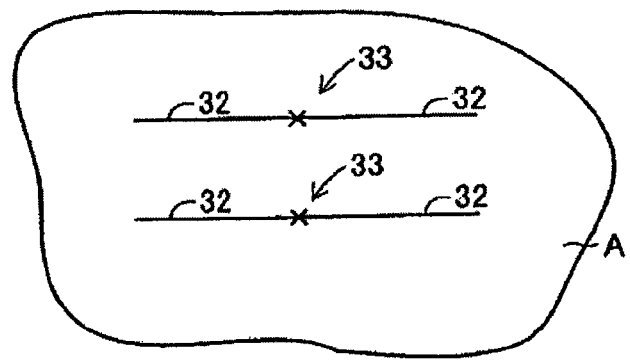
FIG. 15 is a plan view illustrating the state when two sutured parts are formed on the abdominal part.

The method of operation is repeated in the area near suturing tool 30 on the abdomen of the patient, wherein suturing tool 30 has been placed to install the next suturing tool 30. After insertion of the sutures 32, the end parts of sutures 32 of the two suturing tools 30 protruding from the body of the patient are tied together to form sutured part 33, as shown in FIG. 14. This fixes the stomach wall B on the abdominal wall A. Another sutured part 33 is formed by installing the remaining two suturing tools 30 near said sutured part 33, as shown in FIG. 15. With stomach wall B fixed on abdominal wall A, the next operation for installing a gastrostomy tube can be carried out, such as that described in U.S. Pat. No. 6,458,106 of Meier, granted Oct. 1, 2002. After the prescribed operation is finished, each suturing tool 30 is removed from the body of the patient. In this way, a prescribed removing tool (not shown in the figure) is used.

As described above, organopexy tool set S disclosed in this embodiment is comprised of puncture needle 10 for insertion, extruding device 20, and suturing tool 30. The suturing tool 30 is comprised of rod-shaped securing section 31 arranged on the inner side of stomach wall B and suture 32 connected to the center of securing section 31. When securing section 31 is positioned inside stomach wall B, securing section 31 is set along the inner wall of stomach wall B. Securing section 31 and suture 32 form a T, and the free end of suture 32 protrudes from the body. The sutured part 33 is formed to fix stomach wall B on abdominal wall A when a pair of suturing tools 30 are installed on the body of the patient, and the sutures 32 of the two suturing tools 30 are tied together. This simplifies the configuration and use of the suturing tool 30.

A plural of securing sections 31 can be positioned in puncture needle 10 for insertion with the length direction of securing sections 31 aligned with the axial direction of puncture needle 10. These multiple securing sections 31 can be sequentially extruded from the opening at the tip of puncture needle 10 by the extruding device 20. This provides the benefit of not setting the suturing tool 30 in puncture needle 10 each time it is necessary to install a suturing tool 30 on the body of the patient. Instead, the operation can be carried out consecutively for a number of times equal to the number of suturing tools 30 set in puncture needle 10 for insertion. This reduces time and improves results when the organopexy tool S is properly configured.

The four suture exiting holes 24 are formed at intervals around the axis of puncture needle 10. Suture 32 connected to each securing section 31 can protrude from said suture exiting hole 24. Since each suture 32 is positioned in a different part around puncture needle 10 the sutures 32 will not tangle avoiding tearing of the placed suture and patient discomfort.

The force against pressing part 23b is transmitted against the elastic force of coil spring 28 in extruding device 20 causing the spring to compress and store the force. The attachment/detachment pressing section 23 moves downwards along with extruding rod 22. At the point the fastening tool 27 of holding part 26 is pressed against hold releasing part 25b, the extruding rod 22 is released. After the force is released from pressing part 23b, the attachment/detachment pressing section 23 rises under the recovering force or stored force of coil spring 28. The extruding rod 22 is held by friction member 29 to remain stationary during the recovery. By applying a force and releasing a force consecutively, a plural of securing sections 31 can be extruded into the patient's body. By setting the pitch of the movement of attachment/detachment pressing section 23 to the same as the length of securing section 31, each time pressing part 23b is pressed, one securing section 31 can be extruded from the tip part 12 of puncture needle 10 for insertion. This provides for a reliable and repeatable insertion of sutures into a patient's body using the organopexy tool set S.

The organopexy tool set of the present invention is not limited to the aforementioned embodiment. Appropriate modifications can be made. For example, in the aforementioned embodiment, suture 32 of suturing tool 30 is made of nylon. In addition to nylon, the suture can also be made of polyester, silk, polyolefin, etc. Also, the metal used for securing section 31 can be stainless steel, nitinol, titanium, etc. Instead of metal, securing section 31 can also be made of material that is used for suture 32.

In an alternative securing suture, the part of the suture at one end is folded several times at a prescribed length to form a bundle, a core part can be formed, and the suture can be further wound around that core part to constitute a securing section. When the other end of the suture that constitutes the securing section is connected to the suture that constitutes securing section 31, a suturing tool can be formed by one suture. In this way, the suturing tool can be removed easily by un-tying the suture that constitutes the securing section. It is also possible to fix the suture that constitutes the securing section with an adhesive made from a biologically absorptive material that will disappear in the body after a prescribed period of time.

In this case, since the securing section becomes loose and untied after a prescribed period of time since the installation of suturing tool 30, suturing tool 30 can be removed more easily. The shapes and materials of puncture needle 10 for insertion and extruding device 20 can also be modified appropriately. For example, the material of puncture needle 10 for insertion and extruding rod 22 can be stainless steel, nitinol, titanium, etc. The organopexy tool set and organopexy tool disclosed in the present invention are not limited to suturing abdominal wall A and stomach wall B. They can also be used to suture kidneys, bladders, or other internal organs.

Other variations and modifications will be recognized by those of ordinary skill in the art as being within the scope of the present invention.

The invention claimed is:

1. An organopexy tool set (S) comprising a plurality of suturing tools, an extruding device and a puncture needle, each suturing tool having a suture thread and securing section, the puncture needle being sized to accept a plurality of securing sections, wherein a first securing section of the plurality of securing sections is inserted into a patient's body by applying a force to the extruding device and wherein releasing the force applied to the extruding device automatically positions an extruding rod of the extruding device adjacent a second securing section of the plurality of securing sections,
   wherein the extruding device further comprises a cylindrical handle section, the extruding rod, and a pressing section, and
   wherein the extruding device further comprises:
   the extruding rod movable between an interior of the cylindrical handle section and an interior of the puncture needle; and
   a friction member engaging the interior of the cylindrical handle section, the friction member having a through-hole therein for passing the extruding rod under a prescribed frictional force to a pressing part.

2. An organopexy tool set (S) comprising a plurality of suturing tools, an extruding device and a puncture needle, each suturing tool having a suture thread and securing section, the puncture needle being sized to accept a plurality of securing sections, wherein a first securing section of the plurality of securing sections is inserted into a patient's body by applying a force to the extruding device and wherein releasing the force applied to the extruding device automatically positions an extruding rod of the extruding device adjacent a second securing section of the plurality of securing sections,
   wherein the extruding device further comprises a cylindrical handle section, the extruding rod, and a pressing section, and
   wherein the cylindrical handle section comprises a pedestal and a hold releasing part, and
   wherein the organopexy tool set further comprises a fastening tool which comprises a cylindrical fastening part and a flange-shaped fastening release piece, wherein the fastening part is dimensioned to enter a central hole of the pedestal, and
   wherein the fastening tool is pressed by a pressing part of the pressing section and moves towards a tip of a cylindrical body to hold the extruding rod.

3. An organopexy tool set (S) comprising a plurality of suturing tools, an extruding device and a puncture needle, each suturing tool having a suture thread and securing section, the puncture needle being sized to accept a plurality of securing sections, wherein a first securing section of the plurality of securing sections is inserted into a patient's body by applying a force to the extruding device and wherein releasing the force applied to the extruding device automatically positions an extruding rod of the extruding device adjacent a second securing section of the plurality of securing sections,
   wherein the extruding device further comprises a cylindrical handle section, the extruding rod, and a pressing section, and
   wherein the cylindrical handle section comprises a pedestal and a hold releasing part, and
   wherein the organopexy tool set further comprises a fastening tool which comprises a cylindrical fastening part and a flange-shaped fastening release piece, wherein the fastening part is dimensioned to enter a central hole of the pedestal, and wherein the fastening tool is pressed by the hold releasing part and moves closer to a base end than holding pieces on the cylindrical body to release holding of the extruding rod by the holding parts.

* * * * *